(12) United States Patent
Goldhirsch et al.

(10) Patent No.: US 6,455,114 B1
(45) Date of Patent: Sep. 24, 2002

(54) COMPOSITE ABSORBENT STRUCTURE AND METHOD

(76) Inventors: Isaac Goldhirsch, 7 Harimon St., Rehovot (IL), 76343; Steven A. Orszag, 152 Bouvant Dr., Princeton, NJ (US) 08450

( * ) Notice: Subject to any disclaimer, the term of this patent is extended or adjusted under 35 U.S.C. 154(b) by 0 days.

(21) Appl. No.: 09/418,189

(22) Filed: Oct. 13, 1999

(51) Int. Cl.⁷ .................. A61F 13/00; A61L 15/16
(52) U.S. Cl. ............... 428/34.7; 428/34.6; 428/35.2; 428/35.6; 428/72; 428/74; 428/76; 428/35.5; 604/358; 604/367; 604/368; 604/372; 604/378; 604/385.19
(58) Field of Search .............. 428/34.6, 34.7, 428/35.2, 35.6, 72, 74, 76, 35.5; 604/368, 367, 358, 372, 378, 385.19

(56) References Cited

U.S. PATENT DOCUMENTS

| | | |
|---|---|---|
| 3,344,789 A | 10/1967 | Arnold et al. |
| 3,932,322 A | 1/1976 | Duchane |
| 4,055,184 A | 10/1977 | Karami |
| 4,103,062 A | 7/1978 | Aberson et al. |
| 4,105,033 A | 8/1978 | Chatterjee et al. |
| 4,286,082 A | 8/1981 | Tsubakimoto et al. |
| 4,297,410 A | 10/1981 | Tsuchiya et al. |
| 4,327,728 A | 5/1982 | Elias |
| 4,429,001 A | 1/1984 | Kolpin et al. |
| 4,500,670 A | 2/1985 | McKinley et al. |
| 4,573,988 A | 3/1986 | Pieniak et al. |
| 4,699,620 A * | 10/1987 | Bernardin ............... 604/368 |
| 4,699,823 A | 10/1987 | Kellenberger et al. |
| 4,718,899 A * | 1/1988 | Itoh et al. ............... 604/368 |
| 4,721,647 A | 1/1988 | Nakanishi et al. |
| RE32,957 E | 6/1989 | Elias |
| 4,857,065 A | 8/1989 | Seal |
| 4,965,129 A | 10/1990 | Bair et al. |
| 5,002,814 A | 3/1991 | Knack et al. |
| 5,082,723 A | 1/1992 | Gross et al. |
| 5,098,776 A | 3/1992 | Kobayashi et al. |
| 5,147,343 A | 9/1992 | Kellenberger |
| 5,147,345 A | 9/1992 | Young et al. |
| 5,180,622 A | 1/1993 | Berg et al. |
| 5,281,207 A | 1/1994 | Chmielewski et al. |
| 5,324,561 A | 6/1994 | Rezai et al. |
| 5,330,822 A | 7/1994 | Berg et al. |
| 5,354,290 A | 10/1994 | Gross |
| 5,419,956 A | 5/1995 | Roe |
| 5,422,169 A | 6/1995 | Roe |
| 5,433,715 A * | 7/1995 | Tanzer et al. ............... 604/368 |
| 5,489,469 A | 2/1996 | Kobayashi et al. |
| 5,549,590 A | 8/1996 | Suskind et al. |
| 5,985,432 A * | 11/1999 | Wang et al. ............... 604/369 |
| 6,072,101 A * | 6/2000 | Beihoffer et al. ........... 604/368 |

\* cited by examiner

*Primary Examiner*—Rena L. Dye
(74) *Attorney, Agent, or Firm*—Straub & Pokotylo; John C. Pokotylo

(57) ABSTRACT

An absorbent structure and method utilizes pockets or pouches of inorganic or organic granular materials in absorbent structures (such as a structure containing superabsorbents, including polymeric hydrogel forming materials) and fibrous webs, to form a composite heterostructure. The composite absorbent heterostructures are useful, for example, in applications such as diapers, incontinence articles, hygienic supplies and other applications which require good fluid absorbency and retainment properties. The granular material can be made of light plastic materials such as polystyrene or materials such as sand or seeds, and the grains can be hollow, with possible access to their interior volumes.

29 Claims, 4 Drawing Sheets

COMPOSITE ABSORBENT STRUCTURE AND METHOD

FIELD OF THE INVENTION

The invention pertains to a composite absorbent structure and method of making a composite absorbent structure. The invention may be useful in a wide variety of absorbent articles such as, for example, bandages, diapers, diaper inserts, pads hemorrhoid pads, surgical pads, adult incontinence pads, incontinence briefs, training pants, sanitary napkins, tampons, surgical dressings, compresses, hospital underpads, water retaining agents for agricultural and forestry applications, freshness retaining agents for produce and the like.

BACKGROUND OF THE INVENTION

The discovery of polymeric materials that form gels while absorbing fluids has revolutionized the industry of hygienic and medial products as well as other industries in which strongly absorbent articles are needed. Polymers capable of absorbing water in amounts that are tens to hundreds times their own weight are now standardly used in numerous applications. Among the widely used polymers are crosslinked polyacrylates, starch/acrylic acid graft copolymers, ethylene oxide polymers, cellulose derivatives and the like as well as synthetic polymers such as polyvinyl alcohol. The list of polymers and other additives used in this field, including organic and inorganic salts (and odor killers and perfumes), is well known to those familiar with the art of superabsorbent materials.

In spite of the improved fluid holding capabilities of the above-mentioned superabsorbents and significant progress made in improving the physical properties, chemical properties and architecture of absorbent articles, there are still a variety of important unsolved problems encountered in the production, transport, storage and use of such articles.

One of the acute problems in this field is that of "dusting", i.e. the loss of very fine superabsorbent particles in the process of production or shipping of the said articles. Since the superabsorbent material is relatively costly, dusting translates into monetary losses. In addition, this phenomenon leads to a decrease in the efficiency of the absorbent articles since the amount of superabsorbent material is reduced by dusting. Also, the loss of fine particles is not necessarily homogeneous and it thus may give rise to undesired inhomogeneities in the distribution of superabsorbent particles in the product.

Another problem that affects the quality of the absorbent articles is that of "gel blocking". Fine particles tend to coagulate when wet, and they also tend to block capillaries in the web of fibers that disperses (and partly absorbs) the fluid in the product. In addition, the enhanced mobility of fine particles gives rise to inhomogeneities in the distribution of the superabsorbent particles even in the absence of dusting.

Various remedies have been proposed to overcome these problems, such as adding fumed oxides, for example fumed silica or alumina (presumed to be physisorbed on the surfaces of the polymeric particles), in order to decrease the probability for coagulation (cf. e.g. U.S. Pat. No. 3,932,322 in the name of David Duchane); wrapping of the superabsorbent material with a hydrophobic fibrous material (as in U.S. Pat. No. 4,721,647 in the name of Nakanishi et al.) or hydrophilic fibers (as in U.S. Pat. No. 5,489,469 in the name Kobayashi et al.); entangling short fibers with the polymeric particles such that the protruding ends of the fibers promote interaction with the absorbent web in the article thus immobilizing the polymeric particles; embedding the polymeric particles in matrices of fibrous webs (as, e.g., in U.S. Pat. No. 5,147,343 in the name of Kellenberger; or use of interparticle crosslinked aggregates, macroparticles composed of smaller particles of superabsorbent linked together (as, e.g., in U.S. Pat. No. 5,180,622 in the name of Berg et al. or U.S. Pat. No. 5,324,561 in the name of Rezai et al. or in U.S. Pat. No. 5,330,822 in the name of Berg et al.). It is important to notice that while smaller (finer) particles have disadvantages as mentioned above, they have an advantage over large polymeric particles in that the surface areas per volume (or weight) ratio is higher the smaller the particle, and thus their fluid uptake rate is higher. Other ideas put forward in this field include the use of porous polymeric particles (which have internal voids that can communicate with the exterior of the particles. Still other ideas involve the creation of gradients in the degree of capillarity in order to direct the acquired fluid in desired directions. Another idea, proposed in U.S. Pat. No. 4,699,823 in the names of Kellenberg et al., involves the use of gradients in the number density of the superabsorbent particles.

Among the other problems referred to in this field it is important to mention the lateral wicking properties of the absorbent material, the gel strength (under pressure or shear forces) and problems concerning the size and softness of superabsorbent articles and the like. Production problems, such as workability of the materials involved in the process of making the absorbent articles, safety concerns in the production plant as well as safety and comfort of the user are among the other concerns in this field.

SUMMARY OF THE INVENTION

It is an object of the invention to overcome many of the above-noted deficiencies in the prior art, and to provide a novel and unobvious composite absorbent structure and method.

In one aspect, an object of the invention is the utilization of granular material enclosed or substantially enclosed in pervious bags (also referred to as pouches or pockets) in conjunction with an absorbent structure.

In another aspect, it is an object of the invention to increase the mechanical strength of an absorbent article by the provision of a pouch or pouches of granular material.

In another aspect, it is an object of the invention to provide additional space for fluid storage when the superabsorbent particles and the fibrous web are saturated by the provision of a pouch or pouches of granular material.

In another aspect, an object of the invention is the provision of pouches of granular material that are capable of rapid absorption of relatively viscous fluids.

In still another aspect, an object of the invention is the provision of an absorbent article that can actually accumulate more fluid when under pressure or shear forces than without these external forces.

In yet another aspect, an object of the invention is the provision of granular particles that are relatively hard so that external forces exerted on collections of such particles cannot decrease the dimensions of the interparticle pores, and hence such forces cannot squeeze fluid out of the pores.

In another aspect, an object of the invention is the utilization of chemically inert grains, made of, e.g., light plastic materials.

In another aspect, it is an object of the invention to minimize the weight of the granular component by incorporating hollow grains in some embodiments.

In another aspect, it is an object of the invention to provide an absorbent article and method that can serve the additional possible purpose of deodorizing the absorbent article.

In another aspect, it is an object of the invention to incorporate a pouch or pouches of granular matter in absorbent articles containing components such as a water insoluble fibrous web and superabsorbent particles.

With these and other objects, advantages and features of the invention that may become hereinafter apparent, the nature of the invention may be more clearly understood by reference to the following detailed description of the invention, the appended claims, and to the several drawings attached herein.

DETAILED DESCRIPTION OF PREFERRED EMBODIMENTS

Figure 1A:
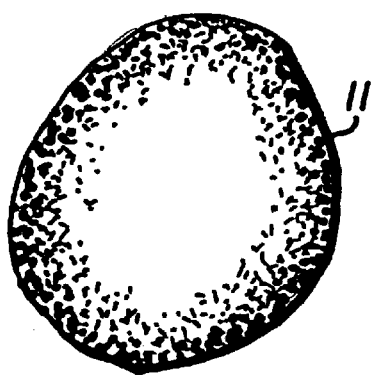
FIG. 1A depicts a relatively smooth granular particle that may be used in an embodiment of the invention.

The invention relates to a composite absorbent structure and method employing granular materials enclosed or substantially enclosed in pockets or pouches utilized in conjunction with other absorbent structures. The combined structure of pouches or pockets with the contained granular material is interchangeably referred to herein as granular pockets and granular pouches. The other absorbent structures may be composed of superabsorbents, such as, for example, polymeric hydrogel forming materials, and/or fibrous webs. Although this specification often refers to articles containing superabsorbent materials as an example of the other absorbent structures, the invention also works in other absorbent structures not having superabsorbents, such as those using only fibrous webs. The term composite heterostructure, when used in this specification, refers to a structure including a pouch or pouches of granular material utilized in conjunction with such another absorbent structure. Composite absorbent heterostructures may be useful in, for example, diapers, incontinence articles, hygienic supplies and other applications which require good fluid absorbency and retainment properties.

An advantage of the composite absorbent heterostructures is that they particularly well-suited for use in absorbent articles or parts of such articles which have to withstand or perform under conditions of enhanced pressure or shear forces. One of the advantages of the pouches of granular materials is the ability to expand under pressure or shear forces (in accordance with the "dilatancy" effect) thus absorbing liquids expelled from the superabsorbent materials; when the external pressure or shear is removed, part of the liquid retained in the pouches of granular material is reabsorbed by the superabsorbent. This dynamic fluid exchange process renders the performance of the composite absorbent heterostructure that includes the granular pouches largely insensitive to external pressure or shear forces. In addition, the granular pouches serve as a means for rapid fluid uptake and distribution (including lateral wicking) when the rate of fluid inflow is high, as they are not hampered by the drawbacks of gel blocking. The granular pouches are also capable of absorbing and distributing high viscosity liquids such as blood and other viscous body exudates. Furthermore, the granular pouches provide temporary storage space when the rate of inflow into the absorbent articles is high, and permanent storage space for fluids when the capacity of the rest of the composite is exceeded.

Another useful property of the composite absorbent heterostructures of the present invention is increased mechanical strength (compared to that of standard absorbent articles) due to the mechanical characteristics of granular materials. The presence of the granular pouches in the aforementioned heterostructures leads to a minimization of leaks even when the absorbent article is under pressure or shear forces, not only because of the aforementioned "dilatancy" effect, but also because the fluid stored in the pores of the granular material is not sensitive to external pressure, which is resisted by the contacts among the granular particles.

In some embodiments, the granular particles required for the purposes of the present invention are inorganic materials. In one preferred embodiment, the particles can be made of light plastic materials such as polystyrene, and they can also be made hollow (with possible access to their interior volumes) so that they do not add significantly to the weight or volume of absorbent articles in which they are used and they do not add idle volumes. In other embodiments, other inorganic particles (such as sand) or organic particles (such as sesame or other seeds) may be used.

In the field of concern here it is common to refer to the superabsorbent (e.g., polymeric) aggregates or to particles which are used as additives (that are, e.g., physisorbed at the surfaces of the superabsorbent particles, as mentioned above) as "particles." However, it is stressed here that the present description differentiates between: (1) the particles which comprise the granular material in the pouches (referred to here interchangeably as grains and granular particles); (2) the superabsorbent particles (which may comprise polymeric superabsorbents); and (3) the additive particles.

In one aspect, the present invention overcomes some of the problems in the field of absorbent articles by capitalizing on the properties of granular materials, in particular on the effect known as dilatancy of granular materials. In brief, collections of discrete granular particles or grains (collectively referred to as granular material) have the property that they expand (dilate) in volume when under pressure or shear forces. It is believed that the physical explanation of the dilatancy effect is that in order to set a granular material into motion the material must expand so that voids into which grains can move are created. Such motion is started by overcoming the frictional links that hold the granular particles together. A familiar effect, which results from the dilatancy mechanism, is the change of appearance of seashore sand when stepped upon (it becomes darker); treading on sand involves exerting pressure on it, causing dilatancy and absorption of water by the sand stepped upon. Without being bound by any particular theory it is reasonable to assume that the penetration of water into dilatant sand (or any other granular material) is due to the combined action of capillarity and pressure driven flow.

The inclusion of granular particles enclosed or substantially enclosed in pervious pouches in an absorbent article offers several advantages. For example, the granular material is capable of rapid acquisition of fluids, including viscous fluids. It is worth reiterating that relatively large superabsorbent particles have low fluid intake rates and relatively small superabsorbent particles (fines) give rise to gel blocking and/or dusting (cf. e.g., U.S. Pat. No. 5,419,956 in the name of Roe) and thus the choice of the size of superabsorbent particles (and their size distribution) is an important issue when both fluid uptake and retention are to be optimized (cf. e.g. U.S. Pat. No. 5,422,169 to Roe). The granular pouches used in the present invention may be capable of rapid fluid uptake and, unless saturated, the granular pouches will not lose fluid, irrespective of the size distribution of the superabsorbent particles and the granular particles.

The utilization of granular pouches provides others advantages regardless of the presence or degree of dilatancy. When applications that involve the exertion of pressure on the absorbent articles are of concern, the granular pouches have the advantage of possessing the dilatancy property, so that the article can actually accumulate more fluid when under pressure or shear forces than without these external forces. Without granular pouches, external forces may squeeze the superabsorbent resulting in a release of accumulated fluid and possible leakage (or surface wetting) of the absorbent article. When pouches containing a dilatant granular material are present, the fluid released by the superabsorbent can then be absorbed by the dilatant granular material within the pouches. Moreover, while state-of-the-art absorbent articles can withstand pressures of the order of 0.01 atmospheres and still partly retain their affectivity as absorbents, granular materials can retain absorbent properties while withstanding pressures of a few atmospheres or more (depending on the strength of material of which the granular particles are made). When the external forcing is removed, capillary forces will move the fluid back to the superabsorbent particles and partially dry the granular material. This process is repeatable, offering a dynamic stabilization of the amount fluid the absorbent article can hold, hence allowing for some insensitivity of the article's properties to external forcing. Although some embodiments of the invention take advantage of the dilatancy effect, the invention is not limited as to requiring dilatancy to be present.

In addition, the granular particles may be selected to be relatively hard and external forces exerted on collections of such particles cannot decrease the dimensions of the interparticle pores, hence such forces cannot squeeze fluid out of the pores. The granular materials selected may also be chosen to be relatively inexpensive. Since the chemical nature of the granular material is irrelevant to the dilatancy effect, one may use chemically inert (preferably hydrophilic) grains, made e.g., of light plastic material (such as hydrophilized polystyrene) or porous grains (e.g., polyvinyl or rayon grains) or hollow grains. A preferred embodiment, which minimizes the weight of the granular material in the composite absorbent heterostructure includes use of granular particles in the form of hollow spherical grains. Granular materials can also help lateral wicking of fluid since they can be made to be relatively homogeneous and isotropic and, even if the grains are relatively small, the enclosure of the grains within the permeable pouches prevents or eliminates "gel blocking" by the grains. Also, the use of granular pouches renders the problem of gel strengths of the superabsorbent particles of less importance than in the absence of such materials; the granular material can actually increase the mechanical strength of the absorbent article without rendering it too brittle or too rigid for use in some applications. Further, granular pouches provide additional space for fluid storage when the superabsorbent particles and/or the fibrous web are saturated. The granular pouches can also be effective in absorbing and distributing relatively viscous fluids.

One may use granular particles having a treated or untreated porous surface in order to partially absorb malodorous materials and/or store perfumes which can be selectively released upon contact with fluids. Also, a properly treated surface of a granular particle and/or microscopic pores therein can be used to trap molecules that are responsible for undesired odors. Thus, the granular material can serve the additional purpose of deodorizing the absorbent article.

It is thus one aspect of the present invention to incorporate pouches of granular material in an other absorbent structure also containing components such as a water insoluble fibrous web and/or superabsorbent particles. The various limitations on, e.g., the dimensions of superabsorbent particles and other properties thereof and of the fibrous web, can be significantly relaxed when granular pouches are utilized with the other absorbent structure. For instance, the use of granular pouches reduces the need to use very narrow superabsorbent particle size distributions (as mentioned above) in order to optimize fluid intake and retention with relatively large densities of superabsorbent particles.

A. The Granular Material

The grains or particles can be made any suitable natural or synthetic material, including, for example, silicon dioxide, polyurethane, polystyrene, acetate. The grains may also be composed of the same materials as additive particles used in surface treating the superabsorbent particles, for example, fumed silica or alumina. The grains may be all of one material or different grain materials may be used in conjunction with one another. The dilatancy effect is not sensitive to the chemical composition of the grains, but the grains preferably should not be too soft so as to prevent collapse of the grains under conditions of external pressure. Any of the above-mentioned and numerous other suitable materials can be used. Chemically inert and nonpoisonous materials (as the above-mentioned) may be preferred for use by human wearers.

Figure 1B:
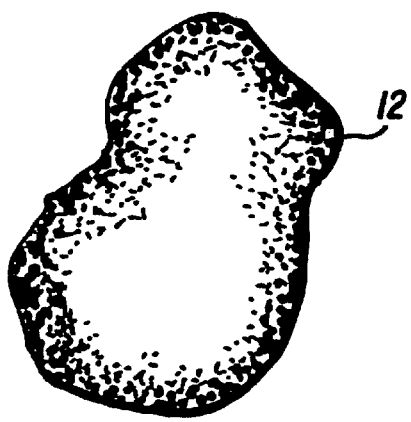
FIG. 1B depicts a corrugated granular particle that may be used in an embodiment of the invention.
Figure 1C:
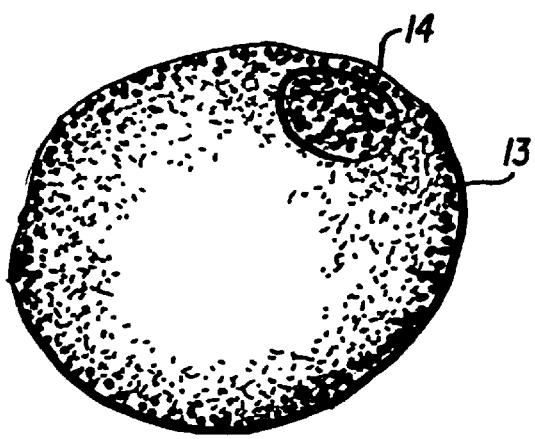
FIG. 1C depicts a hollow granular particle that may be used in an embodiment of the invention.

The shapes and sizes of the grains may be of any suitable shape and size, and may depend on the type of application considered. As illustrated in FIGS. 1A and 1B, the preferred grains are of general (but not precise) spherical or spheroidal shape (with eccentricities preferably between 0.1 and 1). FIG. 1A depicts a typical spheroidal granular particle 11 and FIG. 1B depicts a typical corrugated granular particle 12. Degrees of corrugation may vary from particle type to particle type (or amongst particles of a given type) but even the smoothest industrially made particles may have a finite degree or corrugation. The grains are preferably of linear dimensions ranging from 10 μm to 1000 μm, more preferably in the range of 50 μm to 500 μm, most preferably between 100 μm and 300 μm. Smooth grains are preferable over corrugated grains, and hydrophilic grains are preferable over hydrophobic ones. If hydrophobic grains are used, they should preferably be surface treated to render them hydrophilic, but the present invention can be implemented even if this process is not performed. For the sake of saving weight the grains should preferably be hollow, but solid or porous grains will still perform well. Also, as show in FIG. 1C, hollow grains 13 with openings 14 of typical size of approximately 1 to 500 μm (the size of the opening depending on the particle size) are even more preferable since they can absorb and retain fluids. A preferred hollow granular material is polystyrene.

B. The Granular Pouch

The shapes and sizes of the granular pouches may be of any suitable shape and size, and may depend on the type of application considered. The terms pockets, pouches, bags and enclosures are used interchangeably herein to refer to the enclosures for the granular material. The pouch material can comprise a woven or nonwoven fiber or even (but less preferably) paper (e.g. crepe). The pouch can be thermally sealed, sewn, pattern locked or closed in any other fashion. The pouch material may be either elastic or inelastic.

When diapers or incontinence pads are considered, one may use pouches of linear dimensions ranging from sub-centimeter scale to about 5 cm, the preferred size for a toddler's diaper being about 3 cm and for an adult incontinence pad about 5 cm. When sanitary napkins are considered, the pouches may have lateral dimension of the order of 1 cm and a thickness of about 1 mm.

Figure 2A:
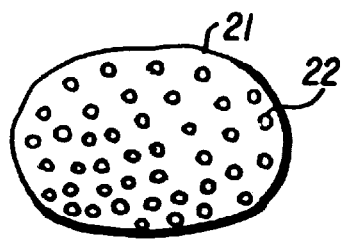
FIGS. 2A, 2B and 2C are side views depicting some alternative profile shapes of pouches of granular material that may be used in an embodiment of the invention.
Figure 2B:
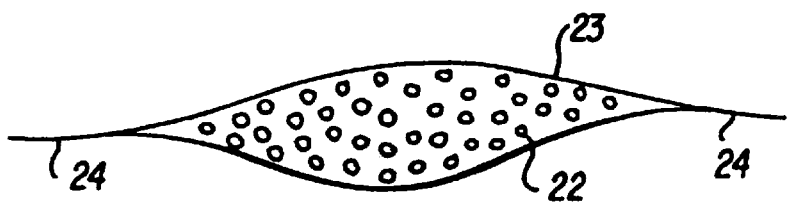
Figure 2C:
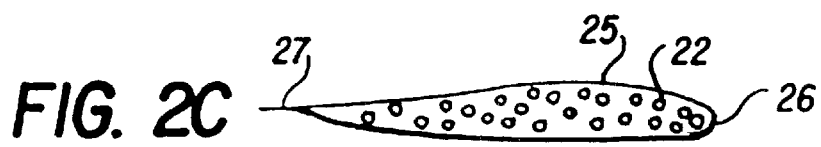

FIGS. 2A, 2B and 2C depict possible shapes of the granular pouches. A preferred embodiment of the pouches uses a permeable and elastic pouch material. FIG. 2A depicts a nearly spherical pouch 21 containing granular particles 22. FIG. 2B depicts a pouch 23, having a tea-bag like shape with sealed ends 24, containing granular particles 22. FIG. 2C depicts another pouch 25 containing granular particles 22 having a tea-bag like shape, with one end 26 folded and the other end 27 sealed. Inelastic and/or partially filled bags (made of other, not necessarily elastic materials) can be used as well. There is no specific limitation on the shapes of the bags for the purposes of the present invention except when it is imposed by the nature of the article in which it is used, for example when it is applied to the design or production of very thin products containing the composite absorbent heterostructures, such as sanitary napkins. In the latter case, nearly flat (up to a few millimeters thick) bags are preferred.

In order to decrease resistance to fluid flow into and out of the bag and also in order to minimize loss of grains (in case of breakage of the bag) in some embodiments it is preferred to attach hydrophilic fibers to the bag, such that one of the ends of each such fiber is inside the bag and the other is outside it. In addition, when the granular pouches are used in a composite absorbent that includes a web of fibers, the ends of the fibers which are outside the bag should preferably be in contact with the web of fibers that extends throughout the article.

Figure 3:
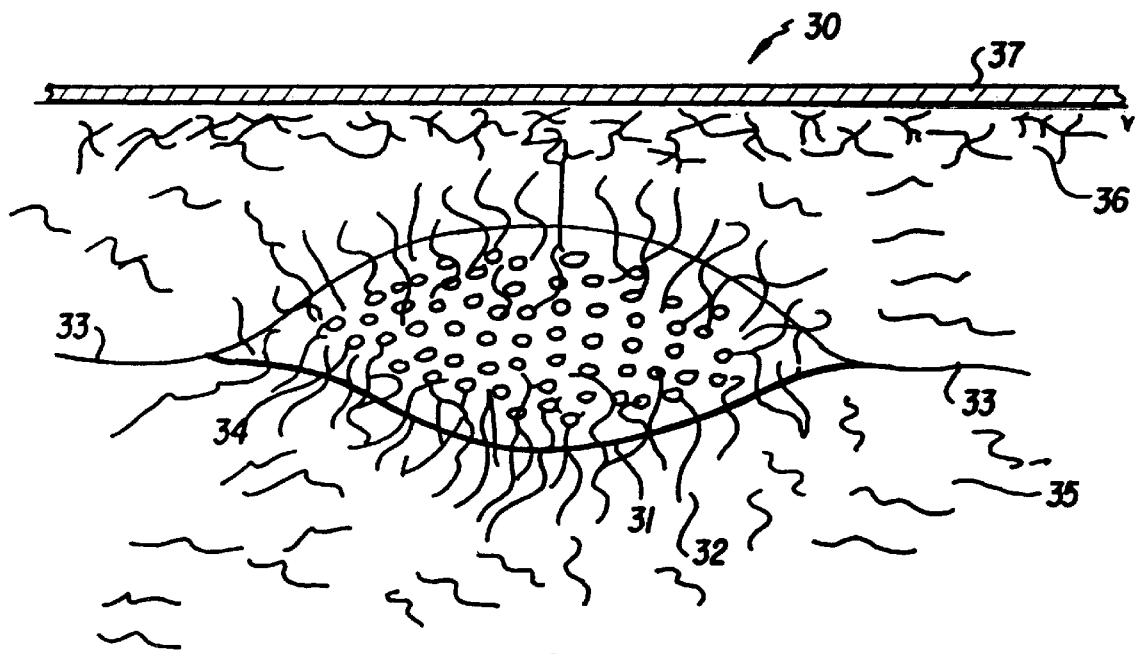
FIG. 3 is a side view which depicts a pouch of granular material with a fibrous web attached thereto that may be used in an embodiment of the invention.

FIG. 3 depicts an alternative embodiment 30 of a granular pouch 31 with a fibrous web 32 attached thereto. The sealed ends of the bag 33 (which contains granular particles 34) are also shown in the figure. As illustrated in FIG. 3, each pouch 31 may be wrapped in hydrophilic fibrous material 32 so as to increase the mobility of fluids between the bag and its surroundings thus promoting the hydrodynamic stabilization of the article. It is preferred that the fluid permeability of the fibers 32 comprising the outside of the bag be lower than that of the surrounding fibers 35 of the absorbent article so that fluid flowing into the article is preferably directed towards the superabsorbent material rather than toward the granular material. For the same reason it is preferable that the resistance to fluid flow of the fibrous web material 36 that is adjacent to the top sheet 37 of, e.g., an article such as a diaper or the outer part of a tampon, be slightly higher than that of the fibrous web 32 surrounding the pouches, and positioned nearer the superabsorbent particles, so that when the superabsorbent particles are squeezed by pressure the fluid is directed to the granular pouches.

C. The Superabsorbent

The superabsorbent particles may be used in a composite absorbent heterostructure according to this invention can be made of any of the standard materials mentioned above as well as of others employed in this field. Examples include, but should not be viewed as limited to, hydrolyzed starch/acrylonitrile graft polymers, partially neutralized starch/acrylonitrile graft copolymers, starch/acrylic acid graft copolymers, partially neutralized starch/acrylic acid graft copolymers, saponified vinyl acetate/acrylic ester copolymers, hydrolyzed acrylonitrile copolymers and any other standardly employed compounds or mixtures thereof. Crosslinked copolymers or crosslinked aggregates of superabsorbent particles are advantageous for immobilization of the superabsorbent particles and better particle-particle hydrodynamic connectivity. It is not necessary to use very narrow superabsorbent particle size distributions although it is preferable to use superabsorbent particle sizes that are larger in diameter than 100 μm to avoid dusting and gel blocking. It is preferred to use superabsorbent particle sizes between 100 μm and 1000 μm, and it is more preferred to use superabsorbent particle sizes between 150 μm and 300 μm, possibly crosslinked in aggregates. Porous superabsorbent particles are practically as efficient as nonporous superabsorbent particles for the purposes of this invention. Additives such as, for example, alumina, silica, bentonite, kaolin, zeolite and other water-insoluble inorganic materials are known to improve the wicking properties of the superabsorbent core. While these or similar such additives are not an absolute necessity for the purposes of the present invention, when they are used it is advantageous to use them with a preferable weight ratio of 1 to 20 percent of the weight of the superabsorbent, most preferably around 5 percent of the superabsorbent. The same additive particles or superabsorbent particles may also be enclosed in pervious pouches such as the pouches described herein, either alone or in combination with other granular particles.

D. The Fiber

For the fibers attached to the granular pouches, such as the fibrous web 32 in FIG. 3, as well as for the fibrous web throughout the article, as discussed herein, any standardly used fibrous material, such as, for example pulp (natural or artificial), cellulose, rayon, vinylon, cotton, wool, cellulose acetate or other materials are adequate. Natural cellulose, pulp and rayon are preferred. Any other suitable fibers may be used.

E. Composite Absorbent Heterostructures

The invention provides for absorbent composite heterostructures, which feature a granular pouch or pouches disposed in an other absorbent structure also utilizing: (1) an absorbent material which may be a superabsorbent material, for example, a gel forming polymer, and/or (2) a fibrous web. It is desirable for the purposes of the present invention that there is good fluid permeability to and from the granular material within the pouches. It is also desirable that the permeability to flow into the superabsorbent material be favorable. It is further desirable to design the absorbent article in such a way that flow from the interior of the article towards the surface is less favorable than flow into the granular pouches and superabsorbent material in order to prevent surface rewetting. This may be achieved by surrounding the granular pouches by hydrophilic fibers which are part of the network of fibers that connects to the superabsorbent particles yet are less resistant to flow than other parts of the fibrous redistribution web. It may be desirable to select specific embodiments such that the maximal distance between a superabsorbent particle and the nearest granular pouch is not too large (about 0.5–5 cm is preferable, 1–2 cm is more preferable). It is further desirable to design the absorbent article so as to prevent excessive surface rewetting under pressure by, for example, including a fibrous network near the surface of the article which is more resistant to flow than the bulk of the fibrous redistribution web.

In the process of production, the granular pouches may, in some embodiments, be inserted in an end product as part of a layer-by-layer production or they may be inserted into the superabsorbent core by mechanical means after the superabsorbent composite, without the granular pouches, has been produced, or they may be inserted into pockets or sections of a quilt-like network of pockets within the absorbent article. In some applications, the preferred weight ratio of the granular pouches to the rest of the composite, in the dry state, is less than 30 percent, more preferably less than 20 percent, most preferably less than 15 percent.

Figure 4:
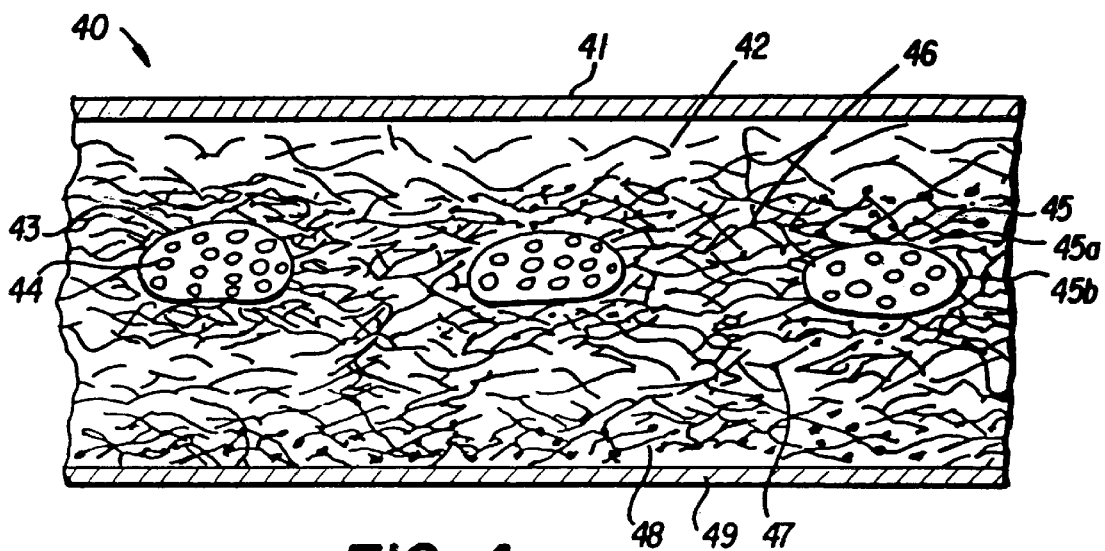
FIG. 4 is a side cross-sectional view that depicts one embodiment of the invention (which may be used as, e.g., a diaper).
Figure 5:
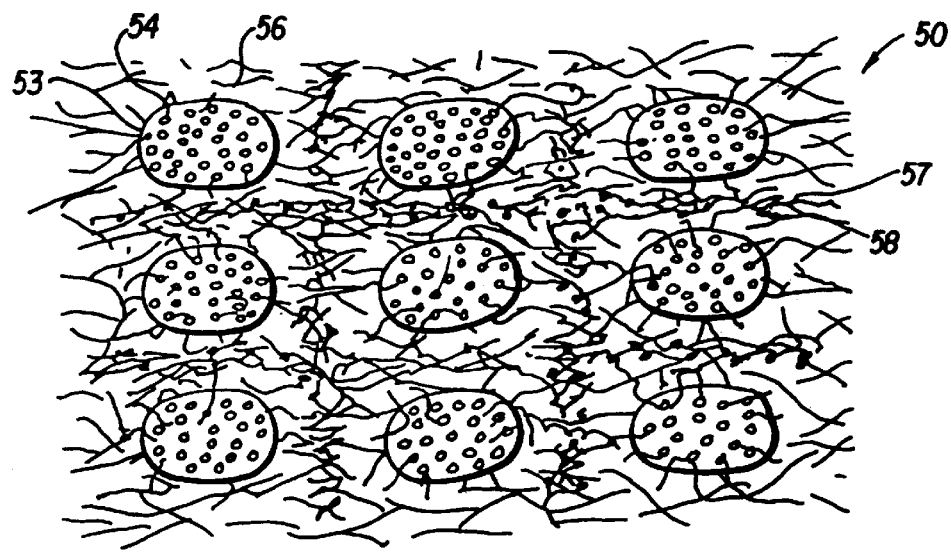
FIG. 5 is a plan view of the embodiment similar to the embodiment of FIG. 4 containing a different superabsorbent/web structure.

FIGS. 4 and 5 depict embodiments that are relevant, for example, for use in articles such as diapers. The embodiment 40 in FIG. 4 has a liquid pervious topsheet 41 below which there is an acquisition/distribution layer of relatively low density fibrous material 42 whose role is to enable rapid fluid uptake and efficient lateral wicking. The granular pouches 43, containing granular particles 44, are positioned below the acquisition/distribution layer and surrounded by a relatively dense web 45 containing fibrous material 45a and superabsorbent particles 45b. For illustrative purposes only, the superabsorbent particles in FIGS. 4–7 are depicted by full, black circles and the granular particles are depicted by open circles. The drawing figures represent the relative placement of the items shown and are not to be taken as being to scale. In the embodiment of FIG. 4, the pouches and the superabsorbent composite surrounding them are separated by a relatively dilute fibrous web 46 that is in contact with a second redistribution layer 47. The various components of the redistribution system are interconnected in this embodiment thus enabling rapid wicking around the granular pouches. A retention layer 48 of superabsorbent particles (which can be much thicker relative to the other layers) is positioned below the pouches. This layer, whose density should usually be higher than that of the superabsorbent web surrounding the granular pouches, should retain most of the fluid when no pressure is exerted on the article or when the fluid—which had entered rapidly and was absorbed by the acquisition layer, the pouches and the superabsorbent material surrounding them—is slowly released and flows, due to a capillarity pressure difference, to the retention layer 48. The lower part of this embodiment can be, for example, a fluid impervious or breathing sheet 49 of the types well known to those familiar with the art of absorbent article design.

FIG. 5 shows a possible plan view of an embodiment 50 that has pouches placed in an arrangement similar to that depicted in FIG. 4 but with a different superabsorbent/web structure. The granular pouches 53 containing granular particles 54 are surrounded by an absorbent fibrous web 56 that partly penetrates them and by a web of fibers 57 containing superabsorbent material 58 (which can be attached and immobilized using methods well known in this field).

Figure 6:
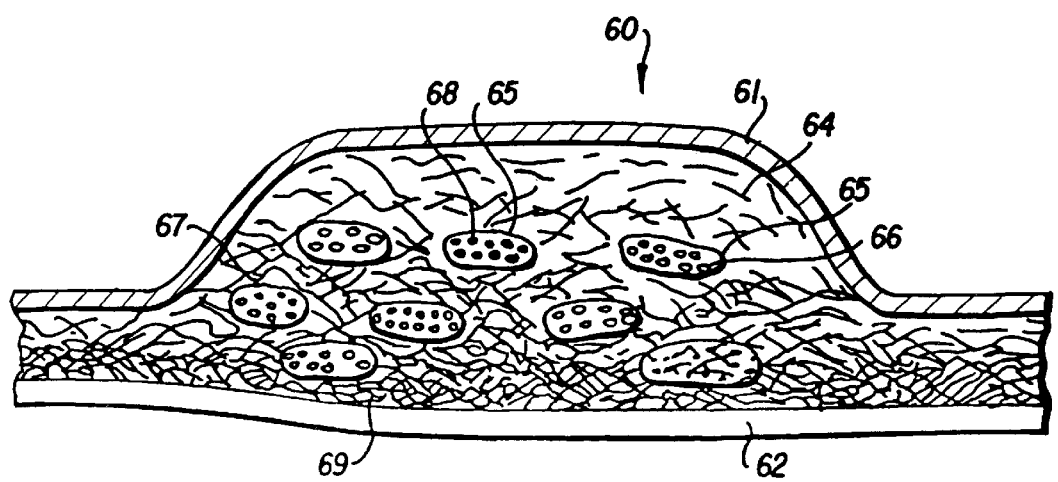
FIG. 6 is a side cross-sectional view that depicts an alternative embodiment of the invention.

FIG. 6 depicts an alternative embodiment 60 which is relevant to use in, for example, a diaper. In this embodiment both the granular particles 66 and the superabsorbent particles 68 are embedded in pouches 65. The embodiment depicted here includes a liquid pervious topsheet 61, a liquid impervious (or 'breathing') backsheet 62, a relatively low density web 63 which comprises the acquisition/distribution layer, a slightly higher density web 64, an even denser layer 67 and a high density absorbent bat 69. This architecture has the advantage of preventing gel blocking due to the swelling and/or migration of the superabsorbent particles, it prevents loss of superabsorbent particles ('dusting') and it enables efficient lateral and vertical wicking. In addition, fluid that is released in rapid gushes can efficiently and rapidly reach the dense fibrous layer 69 from which it is then slowly released (or forced to flow by pressure) into the superabsorbent pouches (or into the granular pouches).

Figure 7:
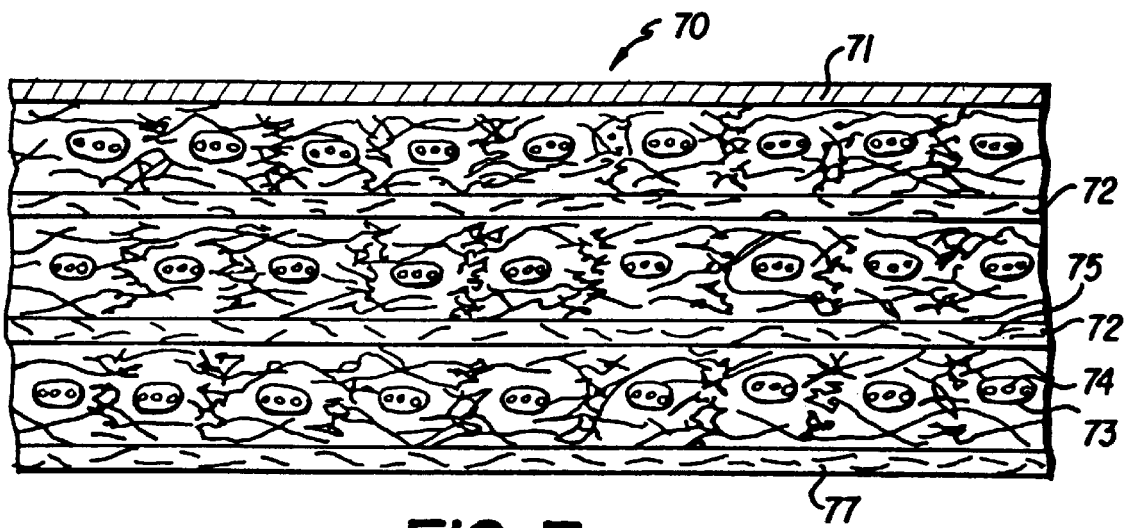
FIG. 7 is a side cross-sectional view that depicts another embodiment of the invention, having multiple layers.

FIG. 7 depicts a multilayer structure 70, useful in, for example, adult incontinence pads. Beneath the liquid pervious top sheet 71 there is an arrangement of layers (for example three, as shown in the figure), each of which is bounded by a wicking/redistribution web such as 72. Inside each layer there are granular pouches 73 containing granular particles 74 and surrounded by a superabsorbent holding web 75. The backsheet layer 77 is fluid impermeable.

Figure 8:
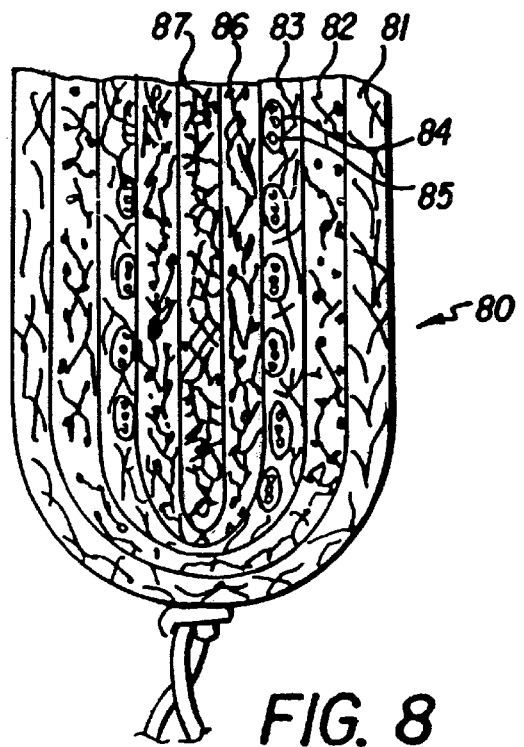
FIG. 8 is a side cross-sectional view of another embodiment of the invention, which is relevant to use in an article such as, for example, a tampon.

FIG. 8 depicts an embodiment 80 that is relevant to use in, for example, a tampon. It includes a fibrous acquisition/redistribution layer 81, a superabsorbent layer 82, a small redistribution layer 83, in which the granular pouches 84 containing grains 85 are embedded, a second superabsorbent layer 86 and a dense fibrous core 87.

The above description and drawings are only illustrative of preferred embodiments which achieve the objects, features and advantages of the present invention, and it is not intended that the present invention be limited thereto. Any modification of the present invention which comes within the spirit and scope of the following claims is considered part of the present invention.

What is claimed is:

1. A composite absorbent heterostructural article, comprising:
   a permeable pouch;
   granular material comprising non-absorbent granular particles and being disposed within said permeable pouch; and
   an absorbent material disposed external to said permeable pouch, wherein the granular material exhibits the dilatancy effect when subjected to external pressure or shear forces.

2. The composite absorbent heterostructural article according to claim 1, wherein said non-absorbent granular material comprises grains having an outer diameter between 100 $\mu$m to 1000 $\mu$m.

3. The composite absorbent heterostructural article according to claim 1, wherein said non-absorbent granular material comprises hydrophylic particles.

4. The composite absorbent heterostructural article according to claim 1, wherein said non-absorbent granular material comprises material selected from the group consisting of plastic grains, sand, and seeds.

5. The composite absorbent heterostructural article according to claim 1, wherein said non-absorbent granular material comprises grains of hydrophilized polystyrene.

6. The composite absorbent heterostructural article according to claim 1, wherein said non-absorbent granular material comprises porous grains.

7. The composite absorbent heterostructural article according to claim 1, wherein said non-absorbent granular material comprises polyvinyl grains.

8. The composite absorbent heterostructural article according to claim 1, wherein said non-absorbent granular material comprises rayon grains.

9. The composite absorbent heterostructural article according to claim 8, comprising at least a portion of said hollow grains wherein each of said grains has one or more apertures defining openings to an interior volume.

10. The composite absorbent heterostructural article according to claim 9, wherein said openings have a diameter of 1 $\mu$m to 500 $\mu$m.

11. The composite absorbent heterostructural article according to claim 10, wherein said openings have a diameter of 1 $\mu$m to 500 $\mu$m.

12. The composite absorbent heterostructural article according to claim 1, further comprising fibers attached to said permeable pouch.

13. The composite absorbent heterostructural article according to claim 12 wherein said superabsorbent material is attached to a fibrous web.

14. The composite absorbent heterostructural article according to claim 13 wherein said superabsorbent material is attached to a fibrous web.

15. The composite absorbent heterostructural article according to claim 13, wherein said superabsorbent comprises a polymeric hydrogel forming material.

16. The composite absorbent heterostructural article according to claim 13, wherein
said fibrous web comprises material selected from the group consisting of natural cellulose, natural pulp, synthetic pulp, and rayon.

17. The composite absorbent heterostructural article according to claim 16, wherein said fibrous web comprises material selected from the group consisting of natural cellulose, natural pulp, synthetic pulp, and rayon.

18. The composite absorbent heterostructural article according to claim 1, wherein said permeable pouch comprises an elastic material.

19. The composite absorbent heterostructural article according to claim 1, wherein said permeable pouch has a maximum width between 1 centimeter and 5 centimeters.

20. A composite absorbent heterostructural article comprising:
a permeable inner sheet;
a fibrous redistribution layer adjacent to said permeable inner sheet;
a plurality of permeable pouches dispersed within said second fibrous layer, each said permeable pouch containing granular material comprising non-absorbent granular particles;
a retention layer comprising an absorbent material adjacent to said second fibrous layer; and,
an outer backing sheet comprising an impermeable material, wherein the granular material exhibits the dilatancy effect when subjected to external pressure or shear forces.

21. The composite absorbent heterostructural absorbent article according to claim 20 wherein said retention layer further comprises a superabsorbent material and a fibrous web.

22. A composite absorbent heterostructural article comprising:
a web of fibrous material;
a plurality of permeable pouches containing absorbent material in conjuction with said fibrous web; and,
a plurality of permeable pouches filled with granular material comprising non-absorbent granular particles imbedded in said fibrous web, wherein the granular material exhibits the dilatancy effect when subjected to external pressure or shear forces.

23. An absorbent article, comprising:
a web of fibrous material;
a plurality of permeable pouches containing absorbent material in conjunction with said fibrous web; and
a plurality of permeable pouches filled with granular material comprising non-absorbent granular particles in conjunction with said fibrous web, wherein the granular material exhibits the dilatancy effect when subjected to external pressure or shear forces.

24. A method of making a composite absorbent heterostructural article comprising the steps of:
providing an absorbent layer in said composite absorbent heterostrucural article; and
providing at least one permeable pouch filled with granular material comprising non-absorbent granular particles imbedded in said absorbent layer, wherein the granular material exhibits the dilatancy effect when subjected to external pressure or shear forces.

25. The method according to claim 24 comprising the additional step of; providing a plurality of alternating absorbent layers and layers comprising permeable pouches filled with non-absorbent granular material.

26. A method of making a composite absorbent heterostructural article comprising the steps of:
providing an absorbent layer in said composite absorbent heterostructural article; and,
providing at least one permeable pouch filled with granular material comprising non-absorbent granular particles imbedded in said absorbent layer, wherein the granular material exhibits the dilatancy effect when subjected to external pressure or shear forces.

27. The method according to claim 26 wherein said permeable pouch is provided within said absorbent layer, and attached to it by said fibrous material.

28. The method according to claim 26 wherein said permeable pouch is provided adjacent to said absorbent layer.

29. A method of making a composite absorbent heterostructural article comprising the steps of:
providing a web of fibrous material;
providing at least one permeable pouch containing absorbent material imbedded in said fibrous web; and
providing at least one permeable pouch filled with granular material comprising non-absorbent granular particles imbedded in said fibrous web, wherein the granular material exhibits the dilatancy effect when subjected to external pressure or shear forces.

* * * * *